US011273119B2

(12) United States Patent
Zewuhn et al.

(10) Patent No.: US 11,273,119 B2
(45) Date of Patent: Mar. 15, 2022

(54) LIPID MIXTURE OF OCTYLDODECANOL AND HYDROGENATED RAPESEED OIL

(71) Applicant: BEIERSDORF AG, Hamburg (DE)

(72) Inventors: Merle Zewuhn, Elmshorn (DE); Dorothe Fiedler, Hamburg (DE); Sepideh Reshad, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 111 days.

(21) Appl. No.: 16/491,212

(22) PCT Filed: Feb. 28, 2018

(86) PCT No.: PCT/EP2018/054879
§ 371 (c)(1),
(2) Date: Sep. 5, 2019

(87) PCT Pub. No.: WO2018/162288
PCT Pub. Date: Sep. 13, 2018

(65) Prior Publication Data

US 2019/0388333 A1 Dec. 26, 2019

(30) Foreign Application Priority Data

Mar. 7, 2017 (DE) ........................ 102017203641.9

(51) Int. Cl.

| | |
|---|---|
| ***A61K 8/92*** | (2006.01) |
| ***A61K 8/02*** | (2006.01) |
| ***A61K 8/34*** | (2006.01) |
| ***A61Q 1/04*** | (2006.01) |

(52) U.S. Cl.
CPC ............ *A61K 8/922* (2013.01); *A61K 8/0229* (2013.01); *A61K 8/342* (2013.01); *A61Q 1/04* (2013.01); *A61K 2800/30* (2013.01); *A61K 2800/43* (2013.01)

(58) Field of Classification Search
None
See application file for complete search history.

(56) References Cited

U.S. PATENT DOCUMENTS

| | | | | |
|---|---|---|---|---|
| 6,552,208 | B1 * | 4/2003 | Alander | A61K 8/922 426/417 |
| 2009/0318554 | A1 | 12/2009 | Kleiman | |
| 2013/0316993 | A1 | 11/2013 | Santus | |
| 2018/0078489 | A1 | 3/2018 | Xu | |
| 2020/0113791 | A1 * | 4/2020 | Manet | A61K 8/342 |

FOREIGN PATENT DOCUMENTS

| | | | |
|---|---|---|---|
| DE | 10210337 | A1 | 9/2003 |
| DE | 20309463 | U1 | 9/2003 |
| DE | 102014204477 | A1 | 9/2015 |
| WO | 9963031 | A1 | 12/1999 |
| WO | 2012131624 | A1 | 10/2012 |
| WO | 2017008243 | A1 | 1/2017 |

OTHER PUBLICATIONS

Database GNPD Mintel Jul. 2013 “Lipstick”.

* cited by examiner

*Primary Examiner* — Nannette Holloman
(74) *Attorney, Agent, or Firm* — Abel Schillinger, LLP

(57) ABSTRACT

Cosmetic lipid mixture of a) octyldodecanol and b) hydrogenated rapeseed oil in a weight ratio of 7:1 to 1:1, process for the production of the lipid mixture, and lipstick containing this lipid mixture.

20 Claims, No Drawings

LIPID MIXTURE OF OCTYLDODECANOL AND HYDROGENATED RAPESEED OIL

BACKGROUND OF THE INVENTION

1. Field of the Invention

The present invention relates to a cosmetic lipid mixture of octyldodecanol and hydrogenated rapeseed oil in a weight ratio of 7:1 to 1:1, a process for the production of the lipid mixture, and a lipstick containing this mixture.

2. Discussion of Background Information

The desire to look beautiful and attractive is by nature ingrained in humans. Even though the ideal of beauty has undergone changes over time, people have always strived to have an immaculate appearance. An essential element of a beautiful and attractive appearance is the condition and appearance of the skin.

In order for the skin to perform its biological functions in full, it needs regular cleansing and care. Skin-care products, usually creams, ointments or lotions, are mostly used to moisturize the skin and replenish its natural oils. Often added to them are active substances that regenerate the skin and are intended, for example, to prevent and reduce its premature aging (e.g. formation of lines and wrinkles).

In addition to the cleansing and care of the skin, cosmetics have an aesthetic role too. They are intended to "improve" the external appearance of the user in accordance with the prevailing cultural perceptions. Cosmetics thus perform a psychological-social function, since they increase the (visual) attractiveness of users. First and foremost among them are "decorative" cosmetics that change the appearance of the user with the aid of coloring agents applied to the skin. However, cleansing and care products have an indirectly beneficial effect too, since a clean, healthy skin is the beauty ideal in humans.

Lip-care products represent a special form of cosmetic preparations. Not only do they help maintain the skin on the lips and protect and regenerate the lips if they become dry and cracked, but lip-care products are also used to provide decoration, as they help create a particular impression through gloss effects or color. Lip-care products come either in stick form or as a cream-like substance ("lip butter") of varying viscosity.

Lip-care products are subject to special requirements. They must be completely safe from a toxicological viewpoint, to exclude any risk of poisoning. In addition, they must be spreadable while at the same time remaining coated on the lips after application without being sticky. Last but not least, such products need to be microbiologically and thermally stable over a long period.

Mineral oils and mineral waxes have since time immemorial been an essential constituent of lip-care products. These have a pleasant, soft, creamy consistency, are odorless and tasteless, and are available in large quantity and high quality at low cost.

A drawback of the prior art is that the use of mineral oils and waxes is not entirely without controversy and has led to review scores for products being marked down in some consumer magazines (e.g. Öko-Test). The reason for this downgrading is that some scientists suspect that mineral oils and mineral waxes may be harmful to health. Even though no adverse effects in humans have come to light despite decades of use of these substances around the world, there is a desire among consumers to avoid preparations containing such ingredients.

It is therefore an object of the present invention to eliminate the disadvantages of the prior art and to develop an alternative lipid base (substitute material) for mineral oils, and for mineral waxes in particular, which have the same sensory and formulation properties as these.

Waxes, in particular mineral waxes, are regularly used in cosmetic preparations as oil binders that fix liquid oil constituents in a paste-like or solid preparation. However, not all oils and waxes are capable of blending together well according to the prior art. Thermal stress or storage for long periods often results in the separation of oil and wax phases. Moreover, these oil-wax mixtures often become either too soft or too hard and brittle, often resulting in the cosmetic losing its desired rheological properties. This is a fundamental problem of lipsticks in particular, particularly during filling of the stick mass.

It is therefore an object of the present invention to develop a lipid mixture into which further oil and wax constituents can be incorporated without problem in a manner that affords thermal and storage stability. In particular, it is an object of the present invention to develop such a lipid mixture that is suitable for lipsticks, i.e. one that is neither too soft to be formulated in stick form nor too hard and brittle for it to be applied to the lips conveniently and in the required amount.

SUMMARY OF THE INVENTION

The objects were surprisingly achieved by a cosmetic lipid mixture of a) octyldodecanol and b) hydrogenated rapeseed oil in a weight ratio of 7:1 to 1:1.

The lipid mixture according to the invention has a pleasantly creamy, soft feel and is odorless and tasteless. It is thermally stable and stable to storage, i.e. phase separation does not occur.

The weight ratio of octyldodecanol to hydrogenated rapeseed oil is according to the invention preferably 3:1 to 1:1 and more preferably 2:1.

Embodiments of the lipid mixture provided by the invention that are advantageous according to the invention are characterized in that the hydrogenated rapeseed oil has a behenic acid content of 35-60% by weight based on the total weight of the hydrogenated rapeseed oil. Preference according to the invention is given to a behenic acid content of 42 to 54% by weight based on the total weight of the hydrogenated rapeseed oil. Particular preference according to the invention is given to a range of between 43 and 45% by weight.

It is according to the invention additionally advantageous if the fatty acid with the second-highest content in the hydrogenated rapeseed oil is stearic acid. The stearic acid content is according to the invention advantageously between 30 and 44% by weight based on the total weight of the hydrogenated rapeseed oil. Particular preference according to the invention is given to a range of between 40 and 42% by weight.

It is according to the invention additionally advantageous if the hydrogenated rapeseed oil contains archidic acid and/or palmitic acid, with a content of both acids being preferable according to the invention.

The advantageous concentration range for archidic acid according to the invention is between 6 and 10% by weight based on the total weight of the hydrogenated rapeseed oil.

The advantageous concentration range for palmitic acid according to the invention is between 2 and 4% by weight based on the total weight of the hydrogenated rapeseed oil.

The invention also provides a process for the production of this lipid mixture which is characterized in that the hydrogenated rapeseed oil is melted in the octyldodecanol with stirring and then cooled with stirring.

The temperature during melting is according to the invention preferably between 60 and 70° C.

The invention also provides a lipid mixture that is produced according to this process.

The invention not least provides a lipstick formulation containing a cosmetic lipid mixture according to the invention or a lipid mixture produced by the process according to the invention and characterized in that the lipstick formulation contains the lipid mixture in a concentration of 40 to 60% by weight based on the total weight of the lipstick preparation. The concentration of the lipid mixture is according to the invention preferably 45 to 55% by weight based on the total weight of the lipstick preparation.

This lipstick formulation provided by the invention is according to the invention advantageously characterized in that the formulation contains further waxes selected from the group of the compounds beeswax, carnauba wax, candelilla wax, sunflower wax, rice wax, hydrogenated castor oil. Preference according to the invention is given to the use of beeswax and carnauba wax.

It is advantageous in the context of the present invention if these further waxes are present in total amounts of 0.05 to 15% by weight based on the total weight of the formulation.

The employed concentrations are according to the invention preferably from 4 to 14% by weight for beeswax, from 0.5 to 2% by weight for carnauba wax, from 0.5 to 5% by weight for candelilla wax, from 0.5 to 5% by weight for sunflower wax, from 0.05 to 2% by weight for rice wax, and from 0.05 to 5% by weight for hydrogenated castor oil, in each case based on the total weight of the lipstick formulation.

For the lipstick formulation provided by the invention, it is additionally advantageous if the preparation contains cetyl palmitate, cetearyl alcohol, and/or shea butter.

In this case it is according to the invention advantageous if the total amount of cetyl palmitate, cetearyl alcohol, and shea butter in the formulation is 0.05 to 15% by weight based on the total weight of the lipstick formulation.

The employed concentrations are according to the invention preferably from 2 to 10% by weight for cetyl palmitate, from 0.5 to 8% by weight for cetearyl alcohol, and from 0.5 to 10% by weight for shea butter, in each case based on the total weight of the lipstick formulation.

Embodiments of the lipstick formulation that are advantageous according to the invention are also characterized in that the formulation contains oils selected from the group of the compounds castor oil, ethylhexyl stearate, coconut glycerides (INCI Cocoglycerides), olive oil, and/or sunflower oil.

The employed concentrations are according to the invention preferably from 5 to 20% by weight for castor oil, from 5 to 30% by weight for ethylhexyl stearate, from 5 to 30% by weight for coconut glycerides, from 1 to 20% by weight for olive oil, and from 1 to 10% by weight for sunflower oil, in each case based on the total weight of the lipstick formulation.

The lipstick formulation provided by the invention may according to the invention advantageously contain pigments. These are then preferably characterized in that the formulation contains 0.001 to 3% by weight of pigments.

Pigments may according to the invention be of organic and inorganic origin, such as organic compounds of the azo-type, indigoids, triphenylmethane-type compounds, anthraquinones, and xanthine dyes, which are known as D&C and FD&C blues, browns, greens, oranges, reds, yellows. Inorganic pigments comprise insoluble salts of certified dyes, which are termed lakes or iron oxides. Examples that may be used are barium lakes, calcium lakes, aluminum lakes, titanium dioxides, mica, and iron oxides. Examples of Al salts that may be used are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake, Blue 1 Aluminum Lake, and combinations.

Examples of known and optionally advantageous iron oxides and hydrated iron oxides are cosmetic yellow oxide C22-8073 (Sunchemical) cosmetic yellow oxide C33-1700 (Sunchemical), cosmetic brown oxide C33-115 (Sunchemical), cosmetic iron oxide red C33-2199 (Sunchemical), cosmetic russet oxide C33-8075 (Sunchemical), cosmetic iron oxide black C33-5000 (Sunchemical), examples of titanium oxides are Kronos 1171 (Kronos) and C47-051 Cosmetic White (Sunchemical).

It is likewise advantageous if these preparations have a content of inorganic pigments selected from the group of metal oxides and/or other metal compounds that are poorly soluble or insoluble in water, preferably oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$), cerium (for example $Ce_2O_3$), mixed oxides of the same metals and mixtures of such oxides and also barium sulfate ($BaSO_4$).

The inorganic pigments may in the context of the present invention advantageously also be used in the form of commercially available oily or aqueous predispersions. These predispersions may advantageously have dispersants or solubilizing agents added to them.

The pigments may according to the invention advantageously be surface-treated ("coated"), with the aim, for example, of forming and maintaining a hydrophilic, amphiphilic or hydrophobic character. This surface treatment may consist of coating the pigments with a thin hydrophilic and/or hydrophobic inorganic and/or organic layer by processes known per se. The various surface coatings may also contain water in the context of the present invention.

Inorganic surface coatings in the context of the present invention may consist of aluminum oxide ($Al_2O_3$), aluminum hydroxide $Al(OH)_3$ and/or hydrated aluminum oxide (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may be present alone, in combination, and/or in combination with organic coating materials.

Organic surface coatings in the context of the present invention may consist of aluminum stearate of vegetable or animal origin, stearic acid of vegetable or animal origin, lauric acid, dimethylpolysiloxane (also: dimethicone), methylpolysiloxane (methicone), simethicone (a mixture of dimethylpolysiloxane with an average chain length of 200 to 350 dimethylsiloxane units and silica gel) or alginic acid. These organic surface coatings may be present alone, in combination, and/or in combination with inorganic coating materials.

It is according to the invention especially preferable if the formulation contains silica, mica or titanium dioxide as pigments.

It is according to the invention advantageous if the lipstick formulation contains hydrophilic constituents in a total amount of 0.001 to 1% by weight based on the total weight of the formulation.

In this case, it is then according to the invention preferable if the formulation contains water, panthenol, and/or glycerol as hydrophilic constituents.

The lipstick formulation provided by the invention is according to the invention advantageously also characterized in that the formulation contains polyglyceryl-3 diisostearate.

In this case, the employed concentration of polyglyceryl-3 diisostearate is according to the invention advantageously from 0.5 to 5% by weight based on the total weight of the formulation.

Embodiments of the lipstick formulation provided by the invention that are advantageous according to the invention are not least characterized in that the formulation contains flavorings (flavoring agents) and/or perfumes.

It is then advantageous according to the invention if the flavoring agents are selected from the group of esters and preferably from the group of acetates and butyrates.

It is according to the invention preferable if isopentyl acetate is used as a flavoring agent.

Embodiments that are advantageous according to the invention are also characterized in that the lipstick formulation contains antioxidants.

Antioxidants considered preferable according to the invention are BHT (butylated hydroxytoluene), tocopherol, and tocopherol acetate.

The lipstick formulation provided by the invention may according to the invention contain further constituents. It is thus according to the invention advantageous if the preparation provided by the invention contains, as further constituents, one or more compounds selected from the group of UV light-protection filters (for example ethylhexyl methoxycinnamate and/or butyl methoxydibenzoylmethane), vitamin A palmitate, vitamin E acetate, allantoin, panthenol, α-bisabolol, lecithin, ceramides, collagens, ubiquinones, and also plant-derived nourishing oils.

It is according to the invention preferable if the lipstick formulation provided by the invention is free of mineral oils.

It is additionally advantageous according to the invention if the preparation is free of polyethylene glycols and derivatives thereof.

Embodiments that are advantageous according to the invention are additionally characterized in that the preparation is free of parabens.

Last but not least, it is advantageous according to the invention if the preparations provided by the invention are free of silicone oils and silicone waxes.

DETAILED DESCRIPTION OF EMBODIMENTS OF THE INVENTION

Examples

The examples shown below are intended to illustrate the present invention without restricting it. Unless indicated otherwise, all amounts shown, proportions, and percentages are based on the weight and the total amount/total weight of the preparations.

a) Lipid Mixture Examples

The hydrogenated rapeseed oil was stirred into the octyldodecanol at 70° C. and cooled to 25° C. with stirring.

Example 1—Lipid Mixture

| | | (%) |
|---|---|---|
| A | Octyldodecanol | 70 |
| B | Hydrogenated Rapeseed Oil | 30 |
| | | 100 |

Example 2—Lipid Mixture

| | | (%) |
|---|---|---|
| A | Octyldodecanol | 85 |
| B | Hydrogenated Rapeseed Oil | 15 |
| | | 100 |

Example 3—Lipid Mixture

| | | (%) |
|---|---|---|
| A | Octyldodecanol | 54 |
| B | Hydrogenated Rapeseed Oil | 46 |
| | | 100 |

b) Examples for the Lipstick Formulation

The lipid mixture and mixing ratio thereof from example 1 were now incorporated into the following stick formulation.

| 1) Solid lip-balm stick | | |
|---|---|---|
| | | (%) |
| A | Octyldodecanol | 35 |
| | Hydrogenated Rapeseed Oil | 15 |
| B | Ethylhexyl Stearate | 15 |
| | Ricinus Communis Seed Oil | 10 |
| C | Butyrospermum Parkii Butter | 2 |
| | Cera Alba | 11.5 |
| | Copernicia Cerifera Cera | 0.5 |
| | Cetearyl Alcohol | 3 |
| | Cetyl Palmitate | |
| D | Polyglyceryl-3 Diisostearate | 3 |
| | Perfume/Flavoring | add to 100 |
| | Pigment | add to 100 |
| | Persea Gratissima Oil | add to 100 |
| | Simmondsia Chinensis Seed Oil | add to 100 |
| | Neohesperidin Dihydrochalcone | add to 100 |
| | UV filter | add to 100 |
| | BHT | add to 100 |
| | | 100 |

Phase A is first heated to approximately 60-70° C., to melt the hydrogenated rapeseed oil into the octyldodecanol.

In a separate beaker, phase B is now heated to 80-90° C.: on reaching this temperature, phase C is added and melted. If these phases and all high-melting waxes have clearly dissolved, they can be cooled down to approximately 60-65° C. Finally, on reaching this temperature, phase A is added, after which the further phase D, for example the emulsifier with the flavoring, may be incorporated.

The mass can now be poured into a mold at approximately 60° C. It should then be allowed to cool down and should not be removed from the mold until fully solidified.

2) Cosmetic stick

| | | (%) |
|---|---|---|
| A | Octyldodecanol | 47 |
| | Hydrogenated Rapeseed Oil | 10 |
| B | Ethylhexyl Stearate | 7 |
| | Ricinus Communis Seed Oil | 10 |
| C | Butyrospermum Parkii Butter | 5 |
| | Candelilla Cera | 0.5 |
| | Cera Alba | 14 |
| | Copernicia Centera Cera | 0.5 |
| | Cetearyl Alcohol | 3 |
| | Helianthus Annuus Seed Cera | 0.5 |
| D | Polyglyceryl-3 Diisostearate | 2.5 |
| | Perfume/Flavoring | add to 100 |
| | Pigment | add to 100 |
| | Panthenol | add to 100 |
| | UV filter | add to 100 |
| | BHT | add to 100 |
| | | 100 |

This is produced in analogous manner to the solid lip-balm formulation.

What is claimed is:

1. A lipstick formulation, wherein the lipstick formulation comprises a lipid mixture of (a) octyldodecanol and (b) hydrogenated rapeseed oil in a weight ratio (a):(b) of from 7:1 to 1:1 in a concentration of from 40% to 60% by weight, based on a total weight of the lipstick preparation.

2. The lipstick formulation of claim 1, wherein the lipid mixture comprises (a) and (b) in a weight ratio of from 3:1 to 1:1.

3. The lipstick formulation of claim 1, wherein (b) has a behenic acid content of from 35% to 60% by weight, based on a total weight of the hydrogenated rapeseed oil.

4. The lipstick formulation of claim 3, wherein (b) has a behenic acid content of from 42% to 54% by weight.

5. The lipstick formulation of claim 3, wherein a fatty acid with the second-highest content in (b) after behenic acid is stearic acid.

6. The lipstick formulation of claim 5, wherein (b) has a stearic acid content of from 30% to 44% by weight, based on a total weight of the hydrogenated rapeseed oil.

7. The lipstick formulation of claim 1, wherein the formulation comprises the lipid mixture in a concentration of at least 45% by weight, based on a total weight of the lipstick preparation.

8. The lipstick formulation of claim 1, wherein the formulation further comprises one or more waxes selected from beeswax, carnauba wax, candelilla wax, sunflower wax, rice wax, and hydrogenated castor oil.

9. The lipstick formulation of claim 8, wherein the one or more waxes are present in a total amount of from 0.05% to 15% by weight, based on a total weight of the formulation.

10. The lipstick formulation of claim 1, wherein the formulation further comprises one or more of cetyl palmitate, cetearyl alcohol, and shea butter.

11. The lipstick formulation of claim 10, wherein a total concentration of cetyl palmitate, cetearyl alcohol and shea butter in the formulation is from 0.05% to 15% by weight, based on a total weight of the formulation.

12. The lipstick formulation of claim 1, wherein the formulation further comprises one or more oils selected from castor oil, ethylhexyl stearate, coconut glycerides (INCI Cocoglycerides), olive oil, and sunflower oil.

13. The lipstick formulation of claim 1, wherein the formulation further comprises from 0.001% to 3% by weight of pigments, based on a total weight of the formulation.

14. The lipstick formulation of claim 13, wherein the formulation comprises one or more of silica, mica and titanium dioxide as pigments.

15. The lipstick formulation of claim 1, wherein the formulation further comprises hydrophilic constituents in a total concentration of from 0.001% to 1% by weight, based on a total weight of the formulation.

16. The lipstick formulation of claim 1, wherein the formulation further comprises one or more of water, panthenol, and glycerol as hydrophilic constituents.

17. The lipstick formulation of claim 1, wherein the formulation further comprises polyglyceryl-3 diisostearate.

18. The lipstick formulation of claim 17, wherein the formulation comprises polyglyceryl-3 diisostearate in a concentration of from 0.5% to 5% by weight, based on a total weight of the formulation.

19. The lipstick formulation of claim 1, wherein the formulation further comprises one or more flavorings (flavoring agents) and/or one or more perfumes.

20. The lipstick formulation of claim 1, wherein the formulation is free of mineral oils.

* * * * *